United States Patent [19]

Meyer

[11] Patent Number: 5,085,658
[45] Date of Patent: Feb. 4, 1992

[54] NEUROSURGICAL PATHOLOGICAL TISSUE REMOVING DEVICE

[75] Inventor: William F. Meyer, Walnut, Calif.

[73] Assignee: Percutaneous Technologies, Walnut, Calif.

[21] Appl. No.: 403,185

[22] Filed: Sep. 5, 1989

[51] Int. Cl.⁵ .............................................. A61B 17/36
[52] U.S. Cl. ...................... 606/46; 606/171
[58] Field of Search ................ 128/6; 606/41, 45, 46, 606/49, 50, 170, 171

[56] References Cited

U.S. PATENT DOCUMENTS

| | | | |
|---|---|---|---|
| 3,618,611 | 11/1971 | Urban | 128/305 |
| 3,821,510 | 6/1974 | Muhcheryan | 219/121 |
| 3,900,022 | 8/1975 | Widran | 128/7 |
| 4,203,444 | 5/1980 | Bonnell et al. | 128/276 |
| 4,543,857 | 10/1985 | Kleinberg et al. | 76/101 |
| 4,550,716 | 11/1985 | Kinoshita | 128/6 |
| 4,598,710 | 7/1986 | Kleinberg et al. | 128/318 |
| 4,620,547 | 11/1986 | Boebel | 128/754 |
| 4,625,713 | 12/1986 | Hiraoka | 128/4 |
| 4,756,309 | 7/1988 | Sachse et al. | 128/305 |
| 4,765,314 | 8/1988 | Kolditz et al. | 128/4 |
| 4,955,882 | 9/1990 | Hakky | 606/170 |

*Primary Examiner*—Max Hindenburg

[57] ABSTRACT

A system of related surgical device used to remove pathological tissue from the central nervous system under continuous, direct visual control, consisting of components which illuminate, provide visualization, use an energy source to resect and remove tissue, protect surrounding normal structures, and control bleeding, while these system components remain in their functional positions during the entire tissue removing process.

9 Claims, 5 Drawing Sheets

NEUROSURGICAL PATHOLOGICAL TISSUE REMOVING DEVICE

BACKGROUND

1. FIELD OF INVENTION

This invention relates to a system of products which are used to remove pathological or abnormal tissue from the area of the central nervous system during a surgical procedure, under direct visual control, including system components which permit establishment of a passageway into the system, creation of a space within the system if one does not normally exist where the tissue removal is to take place, illumination within the space, visualization within the space, an electromechanical cutting device which actually performs the tissue resection, a device to protect surrounding normal tissue from damage during the tissue resection, device to control bleeding if it occurs during the tissue resection, and device to transport the resected tissue from the body without having to remove visualization and tissue resecting devices from their functional position within the central nervous system, during the entire tissue removal process. This typical embodiment is an example of a system of devices which permit removal of tissue from the central nervous system under direct visual control, using any energy source, and specific accessories to make it work effectively.

2. Description of Prior Art

Normal method for surgical removal of pathological tissue from the central nervous system involves major open surgery in which a large incision is made into the scalp, which is retracted to uncover the calvarium, followed by elevation of the periosteum to expose the skull, creation of several burr holes into the skull which are then connected using a saw, and removal of a major portion of the top of the head to access the brain. The area of the brain where tissue is actually to be removed is then approached and the tissue removal occurs. Following this tissue removal, structures within the brain are placed in a relatively normal position, the top of the skull is replaced, the periosteum is sutured into its normal position, and the scalp is placed into its normal position and sutured. This open surgical procedure entails extensive operating time to remove the top of the skull, considerable surgical morbidity as the scalp and skull are incised and subsequently must heal, significant post-operative pain to recover from the surgical wound, and extended time to complete recovery, because of the massive incision into the scalp and skull. Direct cost for medical care and indirect economic opportunity cost because of extended recovery time, and as a result extended absence from a working, productive lifestyle, are significant.

Another method to treat a pathological condition within the central nervous system is to apply radiation therapy. This method is normally used when the general condition of the patient will not permit surgery, when the disease is more diffuse and not localized in one small area, or when location of the disease is such that dissecting to it may cause considerable damage to normal or surrounding structures. Radiation therapy can attenuate diseased tissue, but does not remove the pathological substance, relying on normal body processes to remove the product of the radiation treatment. Although the "target" of radiation therapy can be focused to reduce effect on surrounding, normal tissue, some normal tissue is also destroyed. Radiation therapy has also caused a disease process, known as radionecrosis. Special equipment required to apply radiation therapy is very expensive, which adds to the overall cost of medical care, that is in turn expanding out of control in the country at the present time.

Lasers have been employed to ablate or evaporate pathological substances from the central nervous system, following the establishment of a pathway into the central nervous system to access the pathology and create "line of site" or line of laser energy transmission to the area of athe pathology. Although lasers can effectively evaporate small lesions, the process of debulking larger areas of lesion requires extended operating time, which adds to the cost of medical care and increases patient morbidity, a complication of general surgery. Lasers are very expensive and require special training for effective use, again adding to the cost of medical care.

Hand held instruments have been used to remove pathological substances form the central nervous system. These instruments are either inserted individually or in conjuction with a medical endoscope, through small holes in the head, during a less invasive surgical procedure. Although use of these instruments during this type of surgical technique reduces surgical morbidity, there are several drawbacks including extended operating time as the instruments, which must be very small, have to be constantly removed and cleaned and then reinserted to "bite off" additional chunks of the pathological substance, this process being repeated a significant number of times to remove even small lesions. This is a tedious process for the operating physician, and increases the duration if surgery. The alternative, to employ larger instruments which can bite off larger chunks of tissue at each insertion, dictates accompanying use of a larger instrument insertion cannula, which in turn mandates larger holes be placed onto the skull to accomodate these larger devices.

A search of patent classes 128, 604, and 623 identifies no existing patents which disclose a system of devices used to perform endoscopic removal of pathological tissue from the central nervous system, using an electromechanical cutting device or any other energy source, under continuous direct visual control, and incorporating continuous removal of debris created during the resecting procedure, while device components remain in their functional positions during the entire tissue removing process. However, related prior art for various components of the system described in this patent application include the following.

Prior art are various surgical devices which have been used mainly to remove pathological tissue from within body cavities such as the gastrointestinal system, urinary system, orthopaedic joints, etc. These are either single products, or a series of loosely related devices which are used during the operation but which are not coordinated to optimize their function and are not dependently controlled to produce an optimal effect. These devices include medical optical telescopes to view within a body cavity when used in conjunction with light illuminating products such as a fiber optic light bundle, energy form convertors and energy form transporters which use electrical, mechanical, laser etc. energy to cut, burn, or evaporate pathological tissue, suction devices which aspirate the cut pathological tissue from the body, and tubes used to transport the products of the tissue resecting process from the body cavity.

U.S. Pat No. 1,952,617 discloses an endoscope for viewing within the body during removal of a pathological substance from the genitourinary system. U.S. Pat No. 3,494,354 discloses a flexible endoscope for use in cancer diagnosis. Many additonal prior art devices, both rigid and flexible endoscopes, with the same generic design, have been manufactured to perform surgical procedures on various parts of the body. Although the optical and visualization characteristics of these devices are effective, their functions are not coordinated to other components of the system of products with which they are always used. In addition, these devices, being independently functioning, are not manufactured in a cost effective way, which increases their selling price. This in turn adds to the cost of medical care and the overall cost of health care, that is growing explosively out of control in the United States at the current time.

Various apparata in the surgical art, which remove undesired substances from various parts of the human or animal body, utilizing cutting elements, are disclosed in U.S. Pat Nos. 3,618,611; 3,732,858; 3,743,099; 3,844,272; 4,203,444; 4,274,414; 4,543,857; and 4,598,7120. Electromechanically powered, relatively low speed tissue resecting devices have been employed to perform orthopaedic arthroscopy of the knee, shoulder, wrist, and ankle. These devices have as component of their system, short, medium diameter, rigid cutting blades, or longer larger diameter rigid cutting blades which are inappropriate for use with and through the special design of the neuroendoscope.

Additional apparata in the surgical art which are used to inflow and aspirate fluids when used with endosocpes are disclosed in U.S. Pat. Nos. 3,850,162 and 3,900,022. Other prior art are peristaltic pumps used to inflow liquid into the body. Prior art is a device used to aspirate a liquid from the body. Prior art inflow and suction devices are not controlled and coordinated with each other, as each functions independently of the other.

Related prior art are machines which function independently, including light source illuminators, peristaltic pumps, pneumatically powered tissue resectors, suction machines, electromechanical tissue resectors used for surgical procedures other than indicated in this patent application, laser tissue resectors, electroablation tissue resectors, and ultrasonic energy tissue resectors. These devices are independently controlled. Their functions are not coordinataed with other devices with which they are always used. As a result, they are not manufactured in a cost effective manner and therefore their selling price is greater than a reasonable amount. This adds to the cost of direct medical care which is turn adds to the overall cost of health caare, that is increasing out of control in this country.

Prior art devices are not designed to coordinate functions identified in this invention, including illumination, visualization, electromechanical or other energy source cutting, and transport medium inflow and outflow, within the same operating console, and within the same device that is placed partially within the body. Therefore, these devices do not work as effectively together, extending operating time which also increases cost of medical care.

OBJECTS AND ADVANTAGES

Objects and advantages of the machine described in the present invention are:

(a) to provide a system of devices for removing pathological substances from the central nervous system, including means to illuminate within the system, medical telescope to directly view within the system, electromechanical or other energy source tissue resecting device, means for controlled inflow of a transport medium and aspiration of the combined resected tissue debris and the transport medium during the surgical procedure, and specific accessores to this system of products, which when used as a system allows the maintainence of optical control of the tissue resecting process to assure the process efficiently removes the abnormal tissue, and permitting the medical telescope and tissue resector to remain in their functional positions during the entire tissue removal process, obviating the need to perform major open surgery within the central nervous system and therefore obviating the need to have extended operating time, reducing the patient's pain and suffering from having to remove the entire top of the head and then replacing it, reducing the normal, extensive hospital stay, reducing the normal, extended time to complete recovery, and avoiding the normal, much higher cost for direct medical care;

(b) to provide a means to remove cranial lesions, to evacuate small intracerebral hemotomas, to remove tumors extending into or completely in the ventricle, to perform diagnostic biopsy within the central nervous system, to debulk deep-seated tumors, to remove radionecrotic tissue, to evacuate spontaneous intracerebral hemotomas, to remove cystic brain tumors, and to debulk but not remove cystic tumors, under continuous, direct visual control;

(c) to provide a means for creating a space within the central nervous system, if required;

(d) to provide a means to allow insertion of the medical telescope and electromechanical or other energy source resecting device into the central nervous system, which is small diameter and threfore easily inserted into the central nervous system without having to make a major incision into the system and without having to remove most of the top of the head to perform the surgical procedure, resulting in considerable less pain for the patient;

(e) to provide a means for support of the electromechanical or other energy source tissue resecting device in conjunction with the medical telescope, allowing the resecting device to function properly, and protecting the optical component of the medical telescope from damage during the tissue removal process, permitting direct visual control of the tissue resecting process to assure that pathological tissue is removed and surrounding normal tdissue is not inadvertently removed and resulting in shorter operating time than would be required if hand held instruments or laser energy products were used to perform the tissue resection;

(f) to provide a means for instilling liquid to the end of the electromechanical or other energy source resecting device, to provide a vehicle for transport of debris created during the tissue resecting process, to the outside of the body, obviating the need to constantly remove and clean hand held instruments and resulting in shorter operating time, and reducing operating time in comparison to that required if a laser energy source were used to debulk a larger lesion;

(g) to provide a means for transport of debris create during the tissue resecting process, to the outside of the body;

(h) to provide a means for hemostasis, if required during resection of tissue from the central nervous system;

(i) to provide a means to protect normal tissue from inadvertent damage during removal of pathlolgical tissue from the central nervous system;

(l) to provide a means for coordinated inflow and aspiratiion of the transport medium so the excess liquid is not introduced into the central nervous system during the surgical procedure;

(k) to provide a means to incorporate illumination, visualization, tissue resection, transport medium inflow, debris and transport medium aspiration, normal surrounding tissue protection, and electrocautery to control bleeding, system components, within the same physical structure, part of which is placed within the central nervous system;

(l) to provide an external, interrelated and coordinated system of energy sources and operating controls that control the functions of each of the means indicated above, within the same external physical chasis, including light source, electromechanical or other energy tissue resecting source, electrocautery, and energy source to inflow and control aspiration of a transporting medium, with the chasis modularized for efficient service;

Further objects and advantages are to provide a system of devices whidh will permit the surgeon to remove pathological tissue from the central nervous system, using a medical telescope to visually control the tissue removing process, an electromechanical or any other energy source tissue resecting device, a means to control bleeding during the surgical procedure, a means to protect normal tissue during removal of the abnormal tissue, and related device which deliver a transport medium to the distal end of the tissue resecting device, and then aspirate this medium along with debris created during the tissue resecting process, obviating the need to perform major open surgery, reducing pain, suffering, and discomfort for the patient, reducing the cost of medical care, and also obviating the need to use hand held instruments, laser resectors, or radiothrerapy devices which require greater operating time for effective use, or which do not remove debris created during the treatment process. The system will be relatively inexpensive in comparison to prior art devices which also contributes to lower cost for medical care. Still further objects and advantages will become apparent from a consideration of the ensuring description and drawings.

DESCRIPTION OF THE PREFERRED EMBODIMENT

Figure 1:
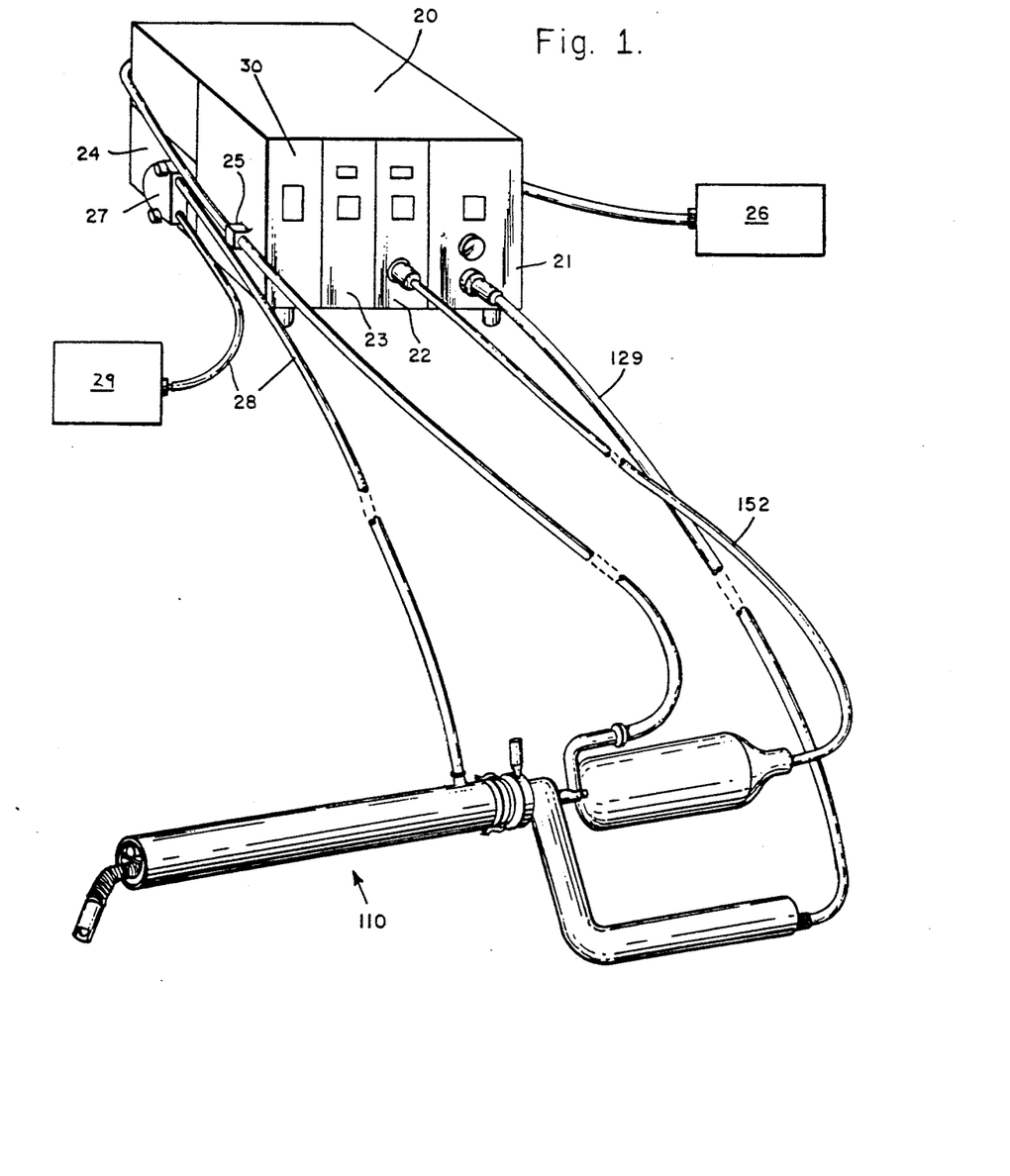
FIG. 1 is a perspective drawing of the endoscopic resecting system which includes a console and the endoscopic viewing and resecting apparatus.

In order to best understand the present invention it is necessary to refer to the following description of its preferred embodiment in conjunction with the accompanying drawing. Referring to FIG. 1 an endoscopic resecting system 10 includes a console 20 and an endoscopic viewing and resecting apparatus 110 for viewing and resecting a target tissue from the central nervous system. The console 20 includes at least five separate modules which are a light source module 21, a motor module 22, a transport medium pump control 23, a transport medium peristaltic pump module 24, and an electrosurgical generator module 30. On the front side of the light source module 21 are its operating controls which include an on/off toggle power switch, a light source intensity digital read-out, an intensity adjusting rheostat, and a fiber optic cable connection. On the front side of the motor module 22 are its operating controls which include an on/off toggle power switch, a motor speed adjustment, and a motor handpiece connection. The electronic components of the motor module 22 include a connection to a 110 volt external power supply, an on/off toggle power switch, a printed circuit board, a transformer, a heat sink, a speed adjusting control and motor handpiece connection. The console 20, which is electrically coupled to a 110 volt external power supply, also includes an on/off toggle power switch, a power supply, a lamp, a lamp cooling fan, a digital read-out of intensity, and a protecting glass and a light intensity measuring device. The non-electronic components of the console 20 also include support brackets for the power supply, the rheostat used to adjust light intensity, the aperture plate, the light attenuator, the fiber optic cable holder and the louvres near the lamp and in line with air flow from the fan.

Still referring to FIG. 1 on the front side of the transport medium pump control module 23 are its operating controls which includes an on/off inflow pump and suction control toggle switch, an inflow rate digital read-out, and inflow rate adjusting rheostat and a suction pressure adjusting rheostat. One the side of the transport medium pumps controls module 23 is a suction tube occluding device 25 which regulates suction pressure from a suctioning apparatus 26. The tube occluding device 25 is adjusted to regulate the outflow of the saline and the resected tissue from the surgical site. The transport medium pump controls module 23 includes a connection to a 110 volt external power supply, an on/off toggle power switch, an inflow rate digital read-out, an inflow rate adjusting rheostat, a printed circuit board for the pump and controls, a printed circuit board for the suction controls, and a suction pressure adjusting rheostat. On the side of the peristaltic pump module 24 is a pump tubing holder 27 which is mechanically coupled to inflow tubing 28. A saline source 29 is fluidly coupled to the inflow tubing 28. The electronic components of the peristaltic pump module 24 includes a connection to pump controls module, a transformer and a motor. The non-electronic conmponents of the peristaltic pump module 24 include a system of torque dampeners, a pump driver, the peristaltic action producing wheel and a mechanical connector from motor shaft to peristaltic action producing wheel. On front side of the electrosurgical generator module 30 its operating controls including power switch and power adjusting rheostat. Also on the front side of the electrosurgical generator module 30 are a grounding plate wire connection, footswitch wire connection, and electrode connection.

Figure 2:
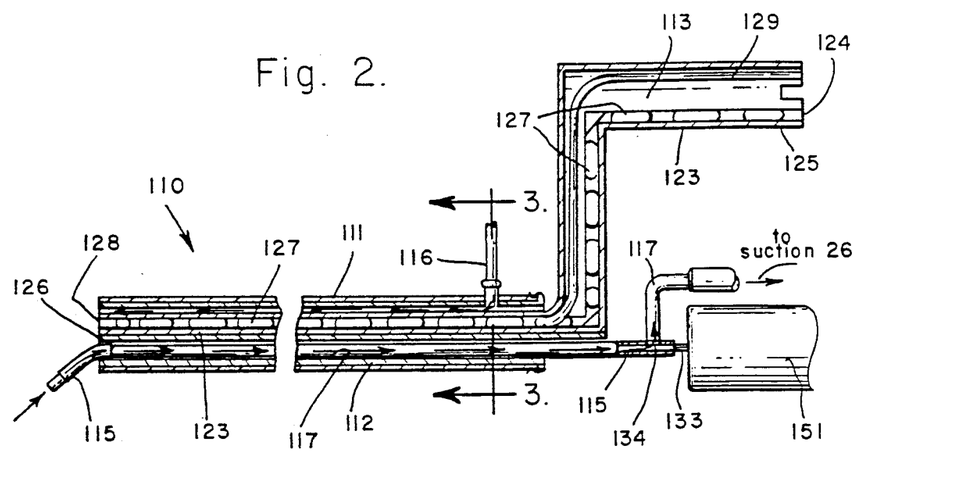
FIG. 2 is a partial longitudinal cross-sectional view of the endoscopic viewing and resecting apparatus of FIG. 1 which includes a compartmentalized tube, a barrier between the compartments of the tube, a visualizing device, an illuminating device and the resecting mechanism.
Figure 3:
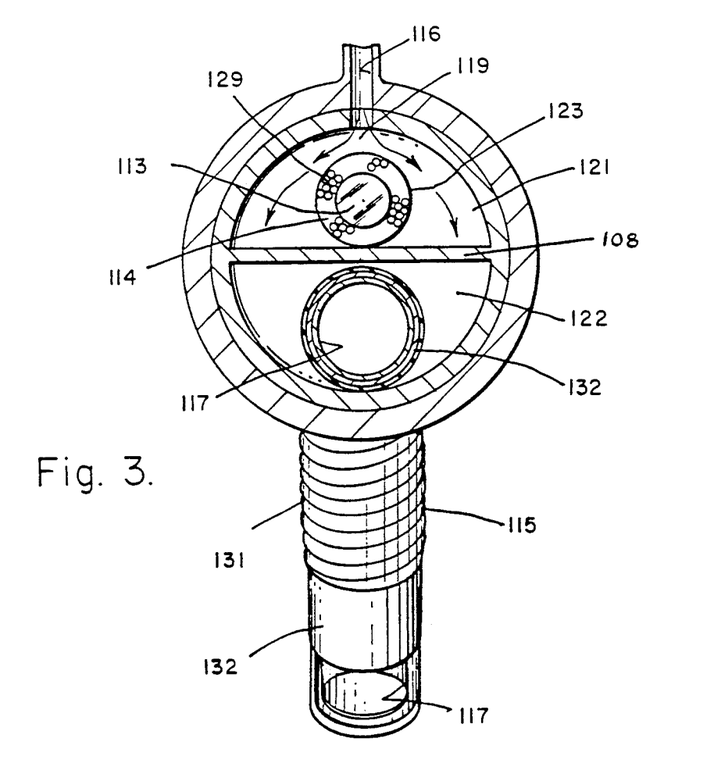
FIG. 3 is a transverse cross-sectional view of the first endoscopic viewing and resecting apparatus of FIG. 1 taken along the line 3—3 of FIG. 2 which also includes a compartmentalized tube, a barrier between the compartments of the tube, an irrigating apparatus and an aspirating outflow apparatus.
Figure 4:
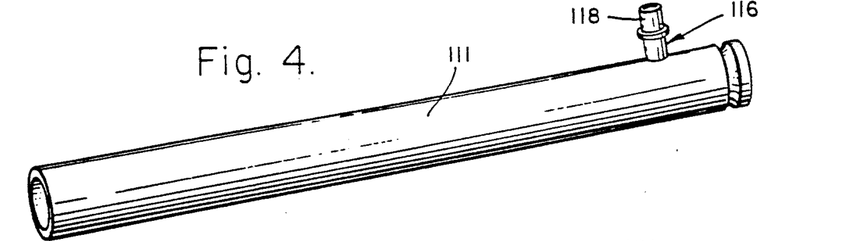
FIG. 4 is a perspective drawing of the sleeve of the endoscopic viewing and resecting apparatus of FIG. 1 into which the compartmentalized tube is inserted.

Referring to FIG. 2 in conjuction with FIGS. 1 and 3 the endoscope viewing and resecting apparatus 110 includes a compartmentalized tube 112, a visualizing device 113, an illuminating device 114, a first resecting mechanism 115, an irrigating apparatus 116, and an aspirating apparatus 117. The suctioning apparatus 26, which is provided in the operating room, is fluidly coupled to the aspirating apparatus 117. The irrigating apparatus 116 has an inflow connector 119 which is mechanically coupled to the compartmentalized tube near its proximal end and which is fluidly and mechancially coupled to the saline source 29 by the inflow tubing 28.

Figure 5:
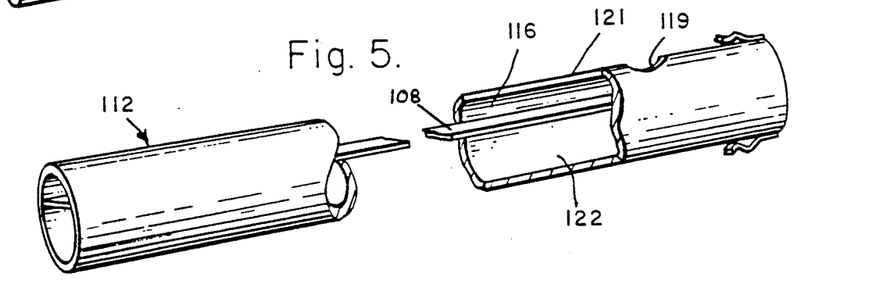
FIG.5 is a partial perspective drawing of the compartmentalized tube and barrier of the endoscopic viewing and resecting apparatus of FIG. 1.
Figures 6, 7:
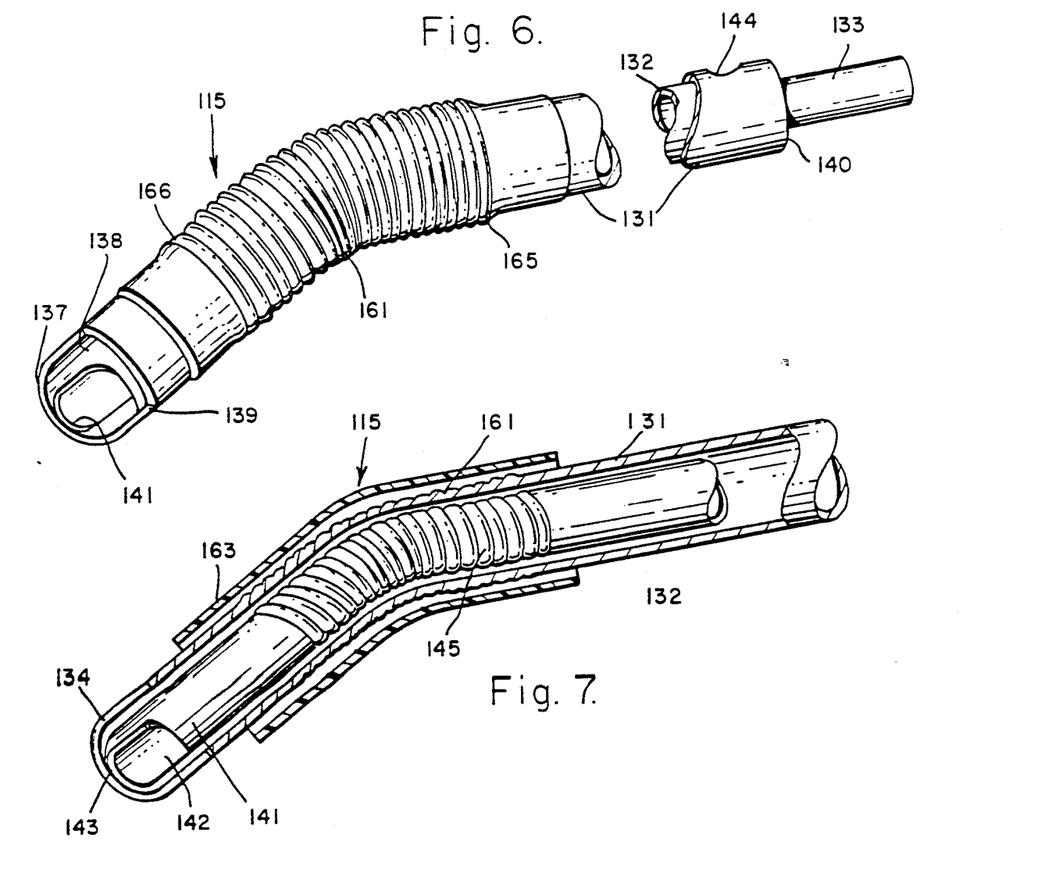
FIG. 6 is a partial perspective drawing of the resecting mechanism of the first endoscopic viewing and resecting apparatus of FIG. 1.
FIG. 7 is a partial longitudinal view in cross-section of the resecting mechanism.
Figure 8:
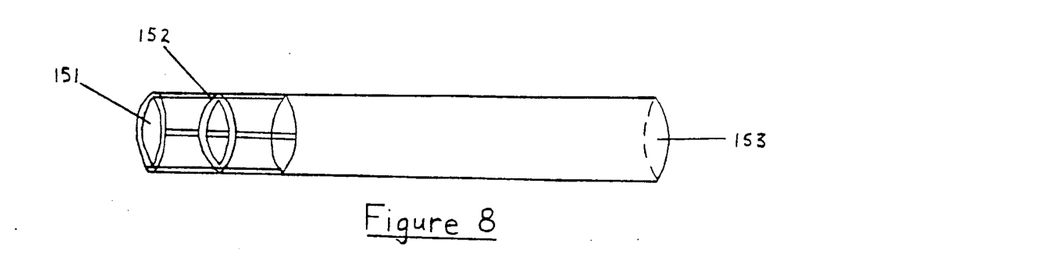
FIG. 8 is a cross-sectional view of the surrounding tissue protecting tube.
Figure 9A:
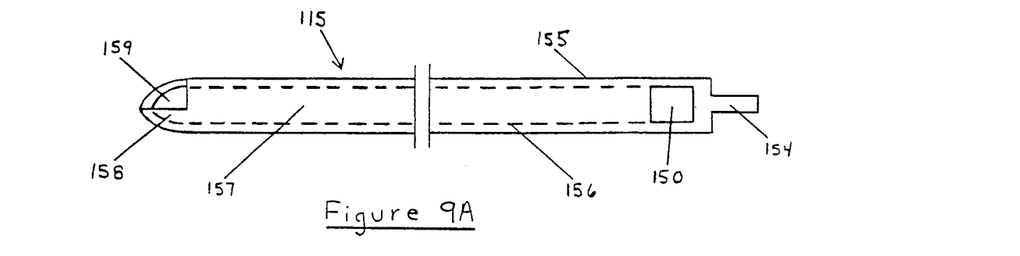
FIG. 9A is a cross-sectional view of an alternative embodiment of the resecting mechanism.
Figure 9B:
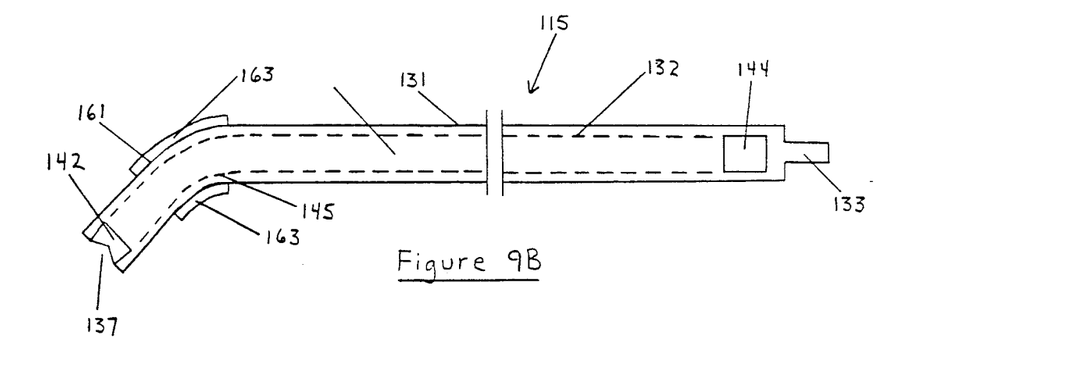
FIG. 9B is a cross-sectional view of the resecting mechanism.
Figure 9C:
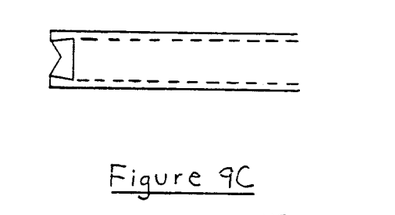
FIG. 9C is a cross-sectional view of only the distal end of an alternative embodiment of the resecting mechanism.
Figure 9D:
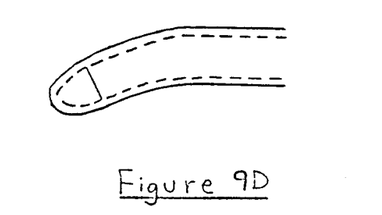
FIG. 9D is a cross-sectional view of only the distal end of the resecting mechanism.
Figure 9E:
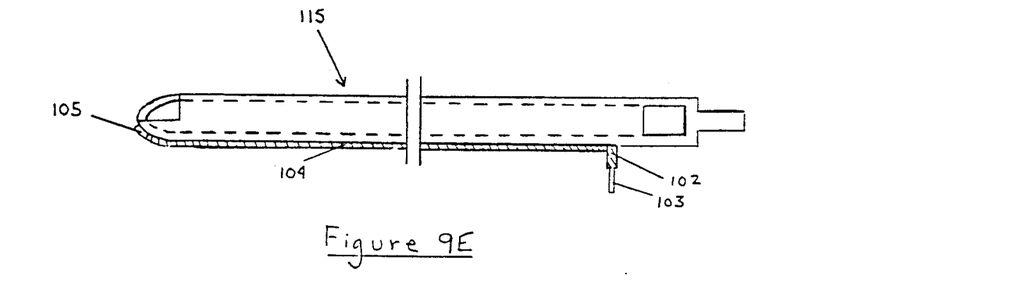
FIG. 9E is a cross-sectional view on another alternative embodiment of the resecting mechanism .

Referring to FIG. 5 in conjunction with FIG. 2 and FIG. 3 the compartmentalized tube 112 has a first compartment 121 of a first set of dimensions, a second compartment 122 of a second set of dimensions larger than the first set of dimensions, and a barrier 108 between the first and second compartments. The visualizing device 113 directly views the target tissue. A portion of the visualizing device 113 is disposed in the first compartment 121. The illuminating device 114 provides illumination of the target tissue. A portion of the illuminating device 114 is disposed in the first compartment 121. The first resecting mechanism 115 resects the target tissue. A portion of the first resecting mechanism 115 is disposed in the second compartment 122. The inlet 116 inlets a transport fluid to the resected target tissue. The outlet 117 outlets the transport fluid to a suctioning device 26. A portion of the outlet 117 is disposed in the second compartment 122. The visualizing device 113, the illuminating device 114, the first resecting mechanism 115, the inlet 116, and the outlet 117, all function is an integrated and coordinated manner. The visualizing device 113 includes a hollow metal sheath 123 and an eyepiece 124. A portion of the hollow metal sheath 123 is disposed in the first compartment 121. The eyepiece 124 is mechanically and optically coupled to the hollow metal sheath 123 at its proximal end 125. The eyepiece 124 is disposed at an angle and adjacent to the resecting mechanism 115. The visualizing device 113 includes a lens train 127 and a forcusing lens 128. The lens train 127 has a plurality of lenses and is mechanically and optically coupled to the eyepiece 124 and disposed in the hollow metal sheath 123. The focusing lens 128 is mechanically and optically coupled to the lens train 127 and disposed in the hollow metal sheath 123 at its distal end 126. In an alternative embodiment the visualizing device 113 may include a coherent optical fiber and a focusing lens. The coherent optical fiber is mechanically and optically coupled to the eyepiece 124 and disposed in the metal sheath 123. The focusing lens 128 is mechanically and optically coupled to the coherent optical fiber and disposed in the metal sheath 123 at its distal end 126. A small video camera may be attached to the eyepiece 124. The illuminating mechanism 114 includes an optical fiber 129 and a light generator 21. A portion of the optical fiber 129 is disposed within the metal sheath 123 parallel to the lens train and is optically aligned with the lens train 127. U.S. Pat. No. 4,601,284, entitled Endoscope Connecting System, issued to Satoshi Arakawa and David H. Cooper on July 22, 1986, teaches a video camera which is optically coupled to an eyepiece, an optical-fiber connector which is disposed orthogonally to the eyepiece and a optical fiber. This is the standard arrangement of the prior art because the optical fiber needed to be out of the way of the surgeon's eye during endoscopy. Most endoscopy is now performed with a video monitor. In the present invention the eyepiece 124 and optical fiber 129 are disposed contiguously and parallel to one another so that a single cable bundle to the console 20 may be used. The light generator 21 generates light and is mechanically and optically coupled to the optical fiber 129. The illuminating device 114 provides illumination of the target tissue. A portion of the illuminating device 114, is disposed in the first compartment 121. The visualizing device 113, the illuminating device 114, the first resecting mechanism 115, the irrigating apparatus 116 and the aspirating apparatus 117 all function in a coordinated manner.

Referring to FIG. 2 in conjuction with FIG. 3, FIG. 5, FIG. 6, FIG. 9A, FIG. 9B, and FIG. 9E, the first resecting mechanism 115 includes or an outer tube 131, an inner tube 132, and driving mechanism 133. The outer tube 131 has a proximal end 136 and a distal end 137 and is disposed in the second compartment 122. The outer tube 131 has a first slot 138 with a first peripheral edge 139 at its distal end 137. The inner tube 132 has a proximal end 140 and a distal end 141 and is disposed coaxially with and rotatively coupled to the outer tube 131. The inner tube 132 has a second slot 142 with a second peripheral edge 143 at its distal end 141 and a window 144 at its proximal end 140. The driving mechanism 133 rotatively drives the inner tube 132 so that the first 139 and second 143 peripheral edge articulate thereby resecting the target tissue. The resected target tissue and transport medium are than aspirated into the lumen 146 of the inner tube 132 at the second slot 142 near the distal end 141 of the inner tube 132. The target tissue moves through the lumen 146 of the inner tube 132 to the window 144 near the proximal end 140 of the inner tube 132. The driving mechanism 133 includes an electric motor 151 and a power cord 152 the distal end of which is connected to the motor module 22. The window 144 is disposed adjacent to the outlet connector 134. The outer tube 131 has a flexible portion 161 which is curved near its distal end 137. The flexible portion 161 has a proximal end 165 and a distal end 166. A plastic material 163 covers the flexible portion of the outer tube 131 from the proximal end 165 to the distal end 166. The inner tube 132 has a flexible portion 145 which is curved near its distal end 141. In an alternative embodiment the first resecting mechanism 115 has an outer tube 155, an inner tube 156 which is disposed coaxially with and rotatively coupled to the outer tube 155, and is straight with no curved portion. The outer tube 155 has a first slot 158 which articulates with a second slot 159 on the inner tube 156, thereby resecting the target tissue. The driving mechanism 154 rotatively drives the inner tube 156 to resect the target tissue. In another embodiment an active electrode 104 is connected from the proximal end 102 of the first resecting mechanism 115 to the distal end 105. A power cord is connected 103 near the proximal end.

Figure 10:
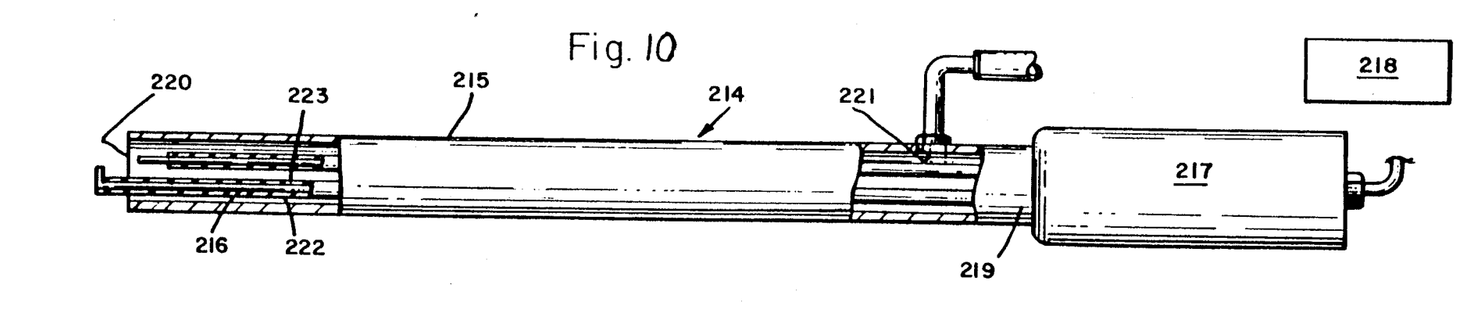
FIG. 10 is a longitudinal view of a second resecting mechanism of a second endoscopic resecting system which includes a console and an endoscopic viewing and resecting apparatus and which has been made in accordance with the principles of the second embodiment of the present invention.

Referring to FIG. 10 a second resecting mechanism 214 includes a tube 215, an active electrode 216, a handpiece 217 and a generator 218. The tube 215 has a proximal end 219 and a distal end 220. A portion of the tube 215 is disposed in the second compartment 122 and has a window 221 at its proximal end 219. The outer surface 222 of the active electrode 216 is coated with a layer 223 of insulating material. A portion of the active electrode 216 is disposed within the tube 215. The active electrode 216 may be either monopolar or bipolar. The generator 218 generates electromagnetic engery in the radio frequency spectrum and is electrically coupled to the active electrode 216 so that the active electrode 216 is heated in order to resect the target tissue. U.S. Pat. No. 4,719,914, entitled Electrosugical Instrument, issued to Gerald W. Johnson on Jan. 19, 1988, teaches an electrosurgical instrument. Each of U.S. Pat. No. 4,562,838, U.S. Pat. No. 3,974,833, U.S. Pat. No. 3,906,955, U.S. Pat. No. 3,828,928 teaches an electrosurgical instrument which has a tube and an electrode for use in high frequency electrocoagulation. The tube either supplies a liquid to the surgical site or aspirates blood and fluid, liquid and/or smoke from the surgical site.

Figure 11:
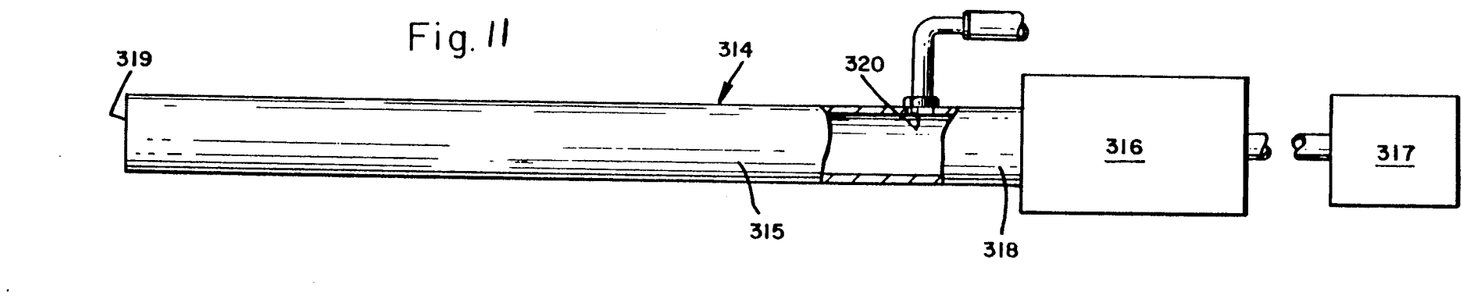
FIG. 11 is a longitudinal view of a third resecting mechanism of third endoscopic resecting system which includes a console and an endoscopic viewing and resecting apparatus and which has been made in accordance with the principles of the third embodiment of the present invention.

Referring to FIG. 11 third resecting mechanism 314 includes a tube 315, a transducer 316 and gererator 317. The tube 315 has a proximal end 318 and a distal end 319 and which is disposed in the second compartment 122. The tube 315 has a window 320 at its proximal end 318. The transducer 316 is mechanically coupled to the tube 314 and disposed at its proximal end 318. The generator 317 generates ultrasonic energy and is electrically coupled to the transducer 316 so that the transducer 316 causes the tube 315 to resonate in order to resect the target tissue. U.S. Pat. No. 4,750,902, entitled Endosopic Ultrasonic Aspirators, issued to David G. Wuchinich, Robert Brendolan, Louis Katz, Donald R. Krawitt on June 14, 1988, teaches an endoscopic ultrasonic aspirator for removal of compliant biological tissue which includes irrigation and aspiration apparatus, a tube and a piezoelectric ultrasonic transducer. U.S. Pat. No. 4,681,561, entitled Ultrasonic Decoupling Sleeve, issued to Larry L. Hood and Maurice M. Imonti on July 21, 1987, teaches a decoupling sleeve for inclusion in a fluid conduit of an ultrasonically-operated surgical instrument. U.S. Pat. No. 4,587,957, entitled Ultrasonic Surgical Device, issued to Yasuo Noguchi and Masaru Shibate on May 13, 1986, teaches an ultrasonic surgical device which includes an ultrasonic transducer and a horn which an irrigation fluid and surgical debris flow from the surgical site.

Figure 12:
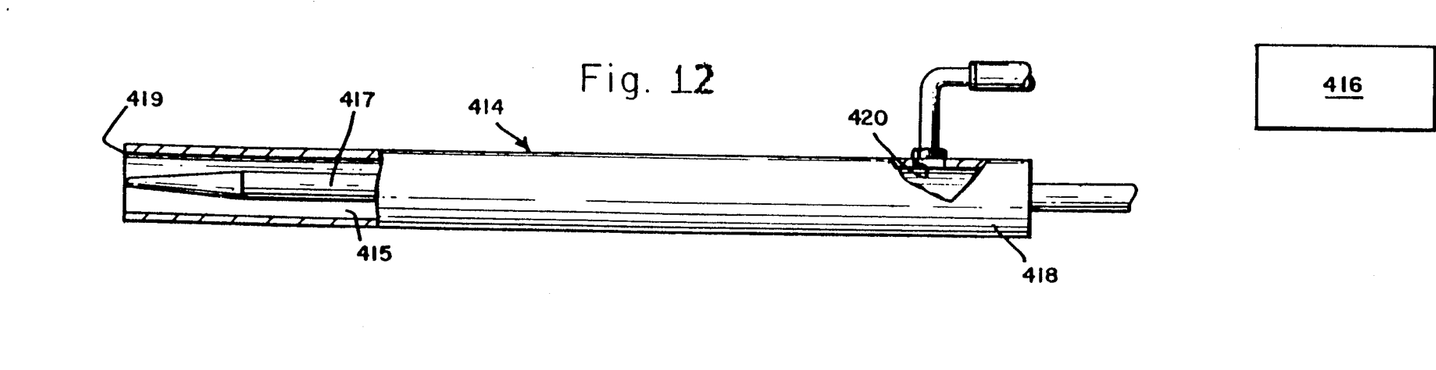
FIG. 12 is a longitudinal view of a fourth resecting mechanism of a fourth endoscopic resecting system which includes a console and an endoscopic viewing and resecting apparatus and which has been made in accordance with the principles of the fourth embodiment of the present invention.

Referring to FIG. 12 a fourth resecting mechanism 414 includes a tube 415, a laser 416, and a lightguide 417. The tube 415 has a proximal end 418 and a distal end 419 and is disposed in the second compartment 122. The tube 415 has a window 420 at its proximal end 418. The laser 416 generates light energy. The light guide 417 is disposed in the tube 415 and guides the light energy so that the conversion of light energy to heat resects the grouting agent or osseus tissue. U.S. Pat. No. 3,528,424, entitled Laser Surgical Knife Equipment, issued to Waldemar A. Ayres on Sept. 15, 1979, teaches a laser generator and a light guide in conjunction with an articulated arm. Although the laser generator of U.S. Pat. No. 3,528,424, is a carbon dioxide laser, other laser generators including, but not limited to, an excimer laser, a ruby laser, an argon laser, an erbium:YAG laser and a neodymium:YAG laser with an without a contact sapphire tip may be used.

Accordingly, the endoscopic resecting system 10 can be used to remove a target tissue from the central nervous system under direct visual control. All of the engery sources for illumination, target tissue removal, and transportation of debris are conveniently located in the same modularized console 20 so that these processes of the operation are controlled and coordinated. The components of the endoscopic resecting system 10 placed partially within the body are organized in order to minimize the outer diameter of the compartmentalized tube 24 while still coordinating all of these functions to efficiently and quickly complete the target tissue removal process.

Direct visual control of the target tissue removal process reduces the need to make large incisions into the body which in turn reduces pain, suffering, and surgical morbidity and also reduces the cost of direct medical care and the overall cost while patients recover from an open operation.

From the foregoing it can be seen that an endosopic resecting system 10 has been described. It should be noted that the sketches are not drawn to scale and that distance of and between the figures are not to be considered significant.

I claim:

1. An endoscopic resecting system for viewing and resecting pathological tissue within the central nervous system, said endoscopic resecting system comprising:

a. a compartmentalized hollow tube with a first compartment of a first set of dimensions, a second compartment of a second set of dimensions larger than said first sets of dimensions and a third compartment of a third set of dimensions smaller than said first sets of dimensions;

b. visualizing means for directly viewing the pathological tissues within the central nervous system, a portion of said visualizing means being disposed in said first compartment;

c. illuminating means for providing illumination of the pathological tissue within the central nervous system, a portion of said illuminating means being disposed in said first compartment;

d. resecting means for resecting the pathological tissue within the central nervous system, a portion of said resecting means being disposed in said second compartment;

e. inletting means for inletting a transport fluid to said resected pathological tissue within the central nervous system, a portion of said inletting means being disposed in said third compartment;

f. electrocoagulating means for controlling bleeding, said electrocoagulating means being disposed in said second compartment;

g. protecting means for protecting normal tissue surrounding the pathological tissue within the central nervous system, said protecting means being disposed externally and mechanically coupled to said compartmentalized hollow tube; and h. outletting means for outletting said transport fluid to the suctioning device, a portion of said outletting means being disposed in said second compartment whereby said visualizing means, said illuminating means, said resecting means, said inletting means and said outletting means all function in an interated and coordinated manner.

2. An endoscopic resecting system for viewing and resecting a pathological tissue within the central nervous system according to claim 1 wherein said visualizing means comprises:

a. a hollow metal sheath which has a proximal end and a distal end and a portion of which is disposed in said first compartment;

b. an eyepiece which is mechanically and optically coupled to said hollow metal sheath at its said proximal end, said eyepiece being disposed at an angle and adjacent to said resecting means;

c. a lens train which has a plurality of lenses and which is mechanically and optically coupled to said eyepiece and disposed in said hollow metal sheath; and a fousing lens which is mechanically and optically coupled to said lens train and disposed in said hollow metal sheath at its said distal end.

3. An endoscopic resecting system for viewing and resecting a pathological tissue within the central nervous system according to claim 2 wherein said illuminating means comprises:

a. an optical fiber a portion of which is disposed within said hollow metal sheath and which is optically aligned with said lens train; and b. a light generating means for generating light which is mechanically and optically coupled to said optical fiber.

4. An endoscopic resecting system for viewing and resecting a pathological tissue within the central nervous system according to claim 1 wherein said visualizing means comprises:

a. hollow metal sheath which has a proximal end and a distal end and a portion of which is disposed in said first compartment;

b. an eyepiece which is mechanically and optically coupled to said hollow metal sheath at its said proximal end, said eyepiece being disposed at an angle and adjacent to said resecting means;

c. a coherent optical fiber which is mechanically and optically coupled to said eyepiece and disposed in said hollow metal sheath; and d. a forcusing lens which is mechanically and optically coupled to said coherent optical fiber and disposed in said hollow metal sheath at its said distal end.

5. An endoscopic resecting system for viewing and resecting a pathological tissue within the central nervous system according to claim 4 wherein said illuminating means comprises:

a. an optical fiber a portion of which is disposed within said hollow metal sheath and which is optically aligned with said coherent optical fiber; and b. a light generating means for generating light which is mechanically and optically coupled to said optical fiber.

6. An endoscopic resecting system for viewing and resecting a pathological tissue within the central nervous system according to claim 1 wherein said resecting means comprises:

a. an outer tube which has a proximal end and a distal end and which is disposed in said second compartment, said outer tube having a first slot with a first peripheral edge at its said distal end;

b. an inner tube which has a proximal end a distal end and which is disposed coaxially with and rotatively coupled to said outer hollow tube, said inner tube having a second slot with a second peripheral edge at its said distal end and a window at its said proximal end; and c. driving means for rotatively driving said inner tube so that said first and second peripheral edge articulate thereby resecting the pathological tissue within the central nervous system.

7. An endoscopic resecting system for viewing and resecting a pathological tissue within the central nervous system according to claim 1 wherein said resecting means comprises:

a. a tube which has a proximal end a distal end and the outer surface of which is coated with a layer of insulating material, a portion of said tube being disposed in said second compartment and having a window at its said proximal end;

b. an active electrode which is coated with a layer of insulating material and a portion of which is disposed within said tube; and c. generating means for generating electromagnetic energy in the radio frequency spectrum, said generating means being electrically coupled to said active electrode so that said active electrode is heated in order to resect the pathological tissue within the cental nervous system.

8. An endoscopic resecting system for viewing and resecting a pathological tissue within the central nervous system according to claim 1 wherein said resecting means comprises:

a. a tube which has a proximal end and distal end and which is disposed in said second compartment, said tube having a window at its said proximal end;
b. a transducer which is mechanically coupled to said tube and disposed at its said proximal end; and
c. generating means for generating ultrasonic energy in the radio frequency spectrum, said generating means being electrically coupled to said tranducer so that said transducer causes said tube to resonate in order to resect the pathological tissue within the central nervous system.

9. An endoscopic resecting system for viewing and resecting a pathological tissue within the central nervous system according to claim 1 wherein said rescecting means comprises:
a. a tube which has a proximal end and a distal end and which is disposed in said second compartment, said tube having a window at its said proximal end;
b. a laser which generates light energy;
c. a light guide is disposed in said tube and is optically coupled to said laser so that conversion of said light energy to heat resects the pathological tissue within the central nervous system.

* * * * *